United States Patent [19]

Hummel-Maquardt et al.

[11] Patent Number: 5,371,000

[45] Date of Patent: Dec. 6, 1994

[54] PROCESS FOR THE PRODUCTION OF ERGOLINE DERIVATIVES

[75] Inventors: Heidi Hummel-Maquardt; Mario Kennecke; Alfred Weber; Klaus Nickisch; Gregor Haffer, all of Berlin, Germany

[73] Assignee: Schering Aktiengesellschaft, Berlin, Germany

[21] Appl. No.: 930,692

[22] PCT Filed: Feb. 6, 1992

[86] PCT No.: PCT/DE92/00088

§ 371 Date: Oct. 7, 1992

§ 102(e) Date: Oct. 7, 1992

[87] PCT Pub. No.: WO92/13857

PCT Pub. Date: Aug. 20, 1992

[30] Foreign Application Priority Data

Feb. 8, 1991 [DE] Germany .................. 4104379

[51] Int. Cl.[5] .................. C12P 17/18; C07D 457/14
[52] U.S. Cl. .................. 435/119; 435/121; 435/886; 546/70
[58] Field of Search .................. 546/70; 435/42, 119, 435/121, 886

[56] References Cited

PUBLICATIONS

Ishii et al. Journal of Chemical Society, Perkin I, 902–905, 1980.
Ishii, H. et al., "Studies on Lysergic Acid Diethylamide and Related Compounds . . . " Chem. Pharm. Bull., 27:12, pp. 3029–3038, 1979.
Chemical Abstracts, 59, No. 3, p. 3099(Yamano et al.), 1962.
Ishii et al., Chem. Pharm. Bull 27(7), vol. 27, pp. 1570–1575, 1979.
Hoffman et al., "Synthesis and LSD-like Discriminative Stimulus Properties . . . " J. Med. Chem, 1985, vol. 28, pp. 1252–1255.

Primary Examiner—Mukund J. Shah
Assistant Examiner—Y. N. Gupta
Attorney, Agent, or Firm—Millen, White, Zelano & Branigan

[57] ABSTRACT

A process for the production of ergoline derivatives of general formula I is described

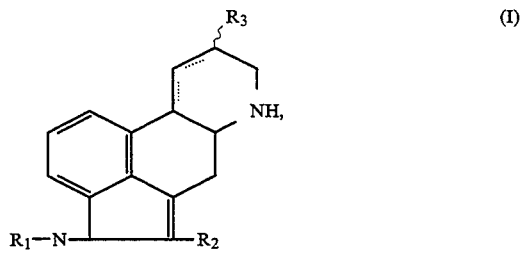

in which the bonds ···· represent two single-bonds or a double bond and a single bond.

$R_1$ means a hydrogen atom or an alkyl group with 1–6 carbon atoms $R_2$ symbolizes a hydrogen atom or an alkyl group with 1–6 carbon atoms, $R_3$ represents a carboxyl group or a grouping of formula $-CONR_4R_5$ or $-NHCQNR_6R_7$ with $R_4$ and $R_5$ meaning hydrogen or an alkyl radical with 1–6 carbons atoms optionally substituted by a hydroxy group and $R_6$ and $R_7$ meaning an alkyl group containing 1–4 carbon atoms and Q meaning an oxygen or sulfur atom.

3 Claims, No Drawings

PROCESS FOR THE PRODUCTION OF ERGOLINE DERIVATIVES

The invention relates to a process for the production of ergoline derivatives of general formula I

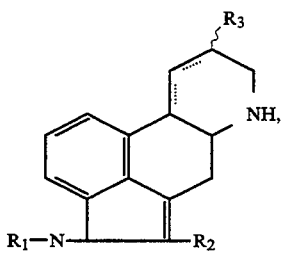

in which the bonds

···· represent two single bonds or a double bond and a single bond.

$R_1$ means a hydrogen atom or an alkyl group with 1-6 carbon atoms $R_2$ symbolizes a hydrogen atom or an alkyl group with 1-6 carbon atoms, $R_3$ represents a carboxyl group or a grouping of formula $$-CONR_4R_5 \text{ or } -NHCQNR_6R_7$$

with $R_4$ and $R_5$ meaning hydrogen or an alkyl radical with 1-6 carbons atoms optionally substituted by a hydroxy group and $R_6$ and $R_7$ meaning an alkyl group containing 1-4 carbon atoms; and Q meaning an oxygen or sulfur atom, which is characterized in that an ergoline derivative of general formula II

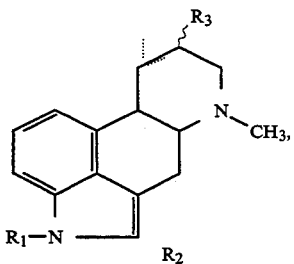

in which

···· $R_1$, $R_2$, $R_3$ have the above-mentioned meaning, is fermented with a bacterial culture of the genus Streptomyces.

The ergoline derivatives of general formula I, as is known, are valuable intermediate products, which can be used, for example, for the synthesis of the pharmacologically effective ergoline derivatives of general formula III

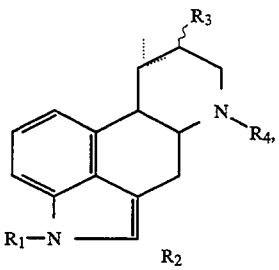

in which

···· $R_1$, $R_2$, and $R_3$ have the above-mentioned meaning and $R_4$ represents an alkyl radical with 2 to 6 carbons atoms (EP-B 0021206; EP-A 0351 352 and J. Med. Chem. 28, 1985, 1252-1255).

The process according to the invention makes it possible to produce the ergoline derivatives of general formula I in a significantly simpler way and under very much more environmentally favorable conditions, than is possible by conventional processes (J. Med. Chem. 28, 1985, 1252-1255).

It has already been mentioned that the process according to the invention is performed with a bacterial culture of genus Streptomyces. In the hitherto performed studies microorganisms Streptomyces purpurascens (DSM 40310) or Streptomyces roseochromogenes (IFO 3363 and IFO 3411) have proved to be suitable; but it is very probable that numerous other cultures of genus Streptomyces can be found that are suitable to perform the process according to the invention.

The process according to the invention is performed under the same fermentation conditions which are also used in the known microbiological conversions of substrates with bacterial cultures.

Under the culture conditions usually used for bacterial cultures—especially those of genus Streptomyces—submerged cultures are cultivated in a suitable nutrient medium with aeration. Then the substrate is added to the cultures (dissolved in a suitable solvent or in emulsified form) and fermented, until a maximum substrate conversion is achieved.

Suitable substrate solvents are, for example, methanol, ethanol, glycolmonomethylether, dimethylformamide or dimethyl sulfoxide or aqueous mineral acids such as phosphoric acid or sulfuric acid. The emulsification of the substrate can be brought about, for example, by injecting the latter in a micronized form or in a water-miscible solvent (such as methanol, ethanol, acetone, glycolmonomethylether, dimethylformamide or dimethyl sulfoxide) dissolved under strong turbulence in (preferably decalcified) water which contains the usual emulsification auxiliary agents. Suitable emulsification auxiliary agents are nonionogenic emulsifiers, such as, for example, ethylenoxy adducts or fatty acid esters of polyglycols. As suitable emulsifiers there can be mentioned as examples the commercially available wetting agents Tegin ®, Tween ® and Span ®.

The optimal substrate concentration, substrate addition period and fermentation time depends on the type of substrate and microorganism used and the fermentation conditions. These values have to be determined, as this is generally necessary in microbiological substrate conversions, in the individual case by preliminary tests, as they are familiar to one skilled in the art.

It is surprising to one skilled in the art that the ergoline derivatives of general formula II are selectively demethylated in the N-6 position under the conditions of the process according to the invention, for one skilled in the art would have had to expect that the substituents in the 8-position of these substrates would also be cleaved.

Indeed from the tests of S. Yamatodani et. al. (Takeda Kenkyusho Nempo 21, 88–94; ref.: C. A. 59, 1963, 3099c) it is basically known that ergoline derivatives can be demethylated in the N-6 position. But these tests were performed with ergoline derivatives that have no cleavable groups in the 8-position (agroclavin and elymoclavin), the substrate concentrations used in these tests are very low. Moreover secondary reactions, such as a hydroxylation in the 8-position, were observed in these reactions so that this process seems to be unsuitable for industrial use.

The following embodiments are used for a more detailed explanation of the process according to the invention.

EXAMPLE 1 a) Spores of *Streptomyces purpurascens* DSM 40310 were applied on agar plates of the following composition:
2% starch
0.4% yeast extract
2% agar
— adjusted to pH 7.2
and incubated 7 days at 30° C. The strain formed reddish to violet substrate mycelium and whitish spores.

b) The spores were elutriated from the plate with 1 ml of physiological NaCl solution and a 500 ml Erlenmeyer flask with 100 medium of the following composition is inoculated with it
0.75% soy meal
0.1% NaCl
0.5% soluble starch
0.65% tris(hydroxymethyl)-aminomethane
0.2 % $K_2HPO_4$
— adjusted to pH 6.2.
The cultivation flask was incubated for 48 hours at 30° C. and 180 rpm.

c) Production of the substrate: 10 g of lysergic acid amide/isolysergic acid amide and 0.5 g of Tween 80 were ground for 1 hour under water cooling in 500 ml of deionized water in the ball mill with corundum spheres (∅ 0.5–1 mm).

d) The fermentation took place in a 2 l flask with 2 flow spoilers and 500 ml of medium of the following composition:
0.75% soy meal
0.1% NaCl
0.5% soluble starch
0.65% tris(hydroxymethyl)-aminomethane
0.2% $K_2HPO_4$
— adjusted to pH 6.2.
The flask was inoculated with 50 ml of culture from the cultivation flask. Then 0.5 g of lysergic acid amide/isolysergic acid amide was added and the flask was incubated for 5 days at 30° C. and 180 rpm.

e) For extraction of the product the culture broth was mixed with 500 ml of 2.1% NaOH and 23% NaCl and shaken out with 1 l of chloroform. The chloroform phase was concentrated by evaporation on a rotary evaporator and then fractionated on a silica gel column (volume 500 ml). Ethylene choride:ethanol: diethylamine in a ratio of 75:25:0.1 was used as the mobile solvent. The fractions, which contain the desired product, were combined, evaporated to dryness and precipitated with ethylene chloride. 0.25 g of 9,10-didehydro-ergolinyl-8α-carboxylic acid amide was obtained. The structure was confirmed by NMR and IR spectroscopy.

EXAMPLE 2

The N-6 demethylation of lysergic acid amide/isolysergic acid amide was performed with *Streptomyces roseochromognes* IFO 3363. The cultivation, substrate production, fermentation and working up took place as indicated in example 1. The yield was close to 0.3 g.

EXAMPLE 3

The N-6 demethylation of lysergic acid amide/isolysergic acid amide was performed with *Streptomyces roseochromogenes* IFO 3411. The cultivation, substrate production, fermentation and working up took place as indicated in example 1. The yield was close to 0.3 g.

EXAMPLE 4

The N-6 demethylation of lisuride took place with *Streptomyces purpurascens* DSM 40310. The cultivation, fermentation and working up was performed as described in example 1.

Production of the substrate: 1 g of lisuride was dissolved in 50 ml of 10% $H_3PO_4$ and sterilized by filtration.

The reaction took place with a yield of 0.4 g of D-3-(9,10-didehydro-8α-ergolinyl)-1,1-diethylurea. The structure was confirmed by NMR and IR spectroscopy.

EXAMPLE 5

The N-6 demethylation of lisuride was performed with *Streptomyces roseochromogenes* IFO 3363. The cultivation, fermentation and working up took place as described in example 1; the substrate production was performed as described in example 4. The yield was close to 0.45 g.

EXAMPLE 6

The N-6 demethylation of terguride took place with *Streptomyces purpurascens* DSM 40310. The cultivation, fermentation and working up was performed as described in example 1. For the production of the substrate 1 g of terguride was dissolved in 50 ml of 10% $H_3PO_4$ and sterilized by filtration.

0.3 g of 1,1-diethyl-3-(8α-ergolinyl) urea was obtained. The structure was confirmed by NMR and IR spectroscopy.

EXAMPLE 7

The N-6 demethylation of terguride was performed with *Streptomyces roseochromogenes* IFO 3411. The cultivation, fermentation and working up was performed as described in example 1; the substrate production was performed as described in example 6. The yield was at about 80% of theory.

We claim:

1. A process for the production of ergoline derivatives of formula I

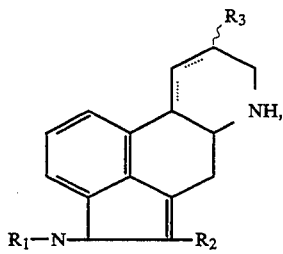

(I)

in which the bonds

····represent two single bonds or a double bond and a single bond, $R_1$ is a hydrogen atom or an alkyl group with 1–6 carbon atoms, $R_2$ is a hydrogen atom or an alkyl group with 1–6 carbon atoms, and $R_3$ is a carboxyl group or a grouping of formula —$CONR_4R_5$ or —$NHCQNR_6R_7$, where $R_4$ and $R_5$ are hydrogen or an alkyl radical with 1–6 carbon atoms optionally substituted by a hydroxy group and $R_6$ and $R_7$ are an alkyl group containing 1–4 carbon atoms and Q is an oxygen or sulfur atom, wherein an ergoline derivative of formula II

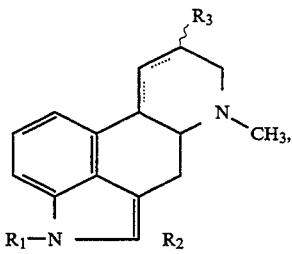

(II)

in which

····$R_1$, $R_2$, $R_3$ have the above-mentioned meaning, is fermented with a bacteria culture selected from the group consisting of *Streptomyces purpurascens* DSM 40310 or *Streptomyces roseochromogenes*, IFO 3363 and *Streptomyces roseochromogenes* IFO 3411, wherein the starting material of formula (II) is selectively demethylated at N-6 position to produce the product of formula (I).

2. The process of claim 1, wherein the starting material of formula (II) is a lysergic acid amide/isolysergic acid amide mixture, lisuride or terguride.

3. The process of claim 1, wherein the bacteria culture is *Streptomyces purpurascens* DSM 40310.

* * * * *